United States Patent [19]

Sweeney et al.

[11] 4,145,368

[45] Mar. 20, 1979

[54] PROCESS FOR THE PRODUCTION OF 1,1,1-TRIFLUORO-2,2-DICHLOROETHANE

[75] Inventors: Richard F. Sweeney, Elma; Bernard Sukornick, Williamsville, both of N.Y.

[73] Assignee: Allied Chemical Corporation, Morris Township, Morris County, N.J.

[21] Appl. No.: 843,759

[22] Filed: Oct. 20, 1977

[51] Int. Cl.$^2$ .............................................. C07C 19/08
[52] U.S. Cl. .................................. 260/653; 260/653.8
[58] Field of Search ...................... 260/653, 653.8, 658

[56] References Cited

U.S. PATENT DOCUMENTS

| | | | |
|---|---|---|---|
| 2,598,411 | 5/1952 | Miller et al. | 260/653 |
| 2,644,845 | 7/1953 | McBee | 260/653 |
| 3,651,156 | 3/1972 | Scherer et al. | 260/653 |

FOREIGN PATENT DOCUMENTS 2144160  3/1973  Fed. Rep. of Germany ........... 260/653

*Primary Examiner*—C. Davis
*Attorney, Agent, or Firm*—Alan M. Doernberg; Jay P. Friedenson

[57] ABSTRACT

1,1,1,-Trifluoro-2-chloroethane (fluorocarbon 133a) is chlorinated with $Cl_2$ and product 1,1,1-trifluoro-2,2-dichloroethane (fluorocarbon 123) is recovered from the reaction mixture, as is overchlorinated byproduct 1,1,1-trifluoro-2,2,2-trichloroethane (fluorocarbon 113a). Fluorocarbon 113a is then reacted in the vapor phase with fluorocarbon 133a in the presence of a catalyst to produce more fluorocarbon 123. Preferred catalysts are activated carbon and especially chromium oxides and oxyfluorides. The product is useful in aerosol, refrigerant and foaming applications, and as an intermediate to other chlorofluoroethanes such as 1,1,1,2-tetrafluoro-1-chloroethane (fluorocarbon 124).

21 Claims, No Drawings

PROCESS FOR THE PRODUCTION OF 1,1,1-TRIFLUORO-2,2-DICHLOROETHANE

BACKGROUND OF THE INVENTION

The present invention relates to the production of chlorofluorocarbons and especially chlorofluoroethanes having a hydrogen.

Chlorofluorocarbons are now widely used as aerosol propellants, refrigerants and foaming agents. The use of perhalogenated chlorofluorocarbons (having no hydrogens), especially as aerosol propellants, has been questioned because of the asserted possibility of damage to the earth's ozone layer. Non-perhalogenated chlorofluorocarbons have been suggested as "stratospherically safe" propellants because of the likelihood that they would decompose in the lower atmosphere.

Non-perhalogenated chlorofluorocarbons may be prepared in one or more steps involving replacement of hydrogens by chlorine or fluorine. Production of the desired non-perhalogenated chlorofluorocarbon is limited, however, by the coproduction of perhalogenated chlorofluorocarbons as byproducts due to the overhalogenation of the starting material. For example, when 1,1,1-trifluoro-2-chloroethane (fluorocarbon 133a according to the ASHRAE designation) is chlorinated with $Cl_2$ by any method, some overchlorinated byproduct 1,1,1-trifluoro-2,2,2-trichloroethane (fluorocarbon 113a) is produced. In the absence of a separate use for fluorocarbon 113a, this overchlorination detracts from the overall yield of fluorocarbon 123 based upon both hydrocarbon starting material and halogen reactants. It has now been surprisingly found that the fluorocarbon 113a byproduct can be converted to the fluorocarbon 123 product without the introduction of new reactants into the overall process or significant increases in the halogen waste byproduct stream.

The disproportionation of fluorochlorocarbons is well known in the art. The disproportionation reaction involves an exchange of chlorine and fluorine leading to more highly fluorinated compounds and to compounds of lower fluorine but higher chlorine content. In general, complex mixtures are formed since the disproportionation reaction theoretically can be repeated until compounds having only chlorine atoms and fluorine atoms are left in the mixture. In general, the disproportionation usually does not proceed to this ultimate end.

In contrast to prior art disproportionations, the reaction of the subject invention involves a chlorine-hydrogen exchange in which fluorocarbon 113a gives up a chlorine atom and receives a hydrogen and fluorocarbon 133a gives up a hydrogen and receives a chlorine.

BRIEF DESCRIPTION OF THE INVENTION

The present invention includes a process for producing 1,1,1-trifluoro-2,2-dichloroethane comprising chlorinating 1,1,1-trifluoro-2-chloroethane with $Cl_2$, recovering product 1,1,1-trifluoro-2-dichloroethane from the reaction mixture, reacting in the vapor phase overchlorinated byproduct 1,1,1-trifluoro-2,2,2-trichloroethane in the reaction mixture with additional 1,1,1-trifluoro-2-chloroethane in the presence of a metal oxide or activated carbon catalyst and recovering additional 1,1,1-trifluoro-2,2-dichloroethane from the catalyst reaction mixture.

The present invention also includes a process for producing 1,1,1-trifluoro-2,2-dichloroethane by reacting in the vapor phase 1,1,1-trifluoro-2-chloroethane with 1,1,1-trifluoro-2,2,2-trichloroethane in the presence of a catalyst selected from the group consisting of chromium oxides and oxyfluorides and activated carbon.

DETAILED DESCRIPTION OF THE INVENTION

The present invention includes a process for manufacturing 1,1,1-trifluoro-2,2-dichloroethane (hereinafter referred to as fluorocarbon 123 or merely 123) by reaction of 1,1,1-trifluoro-2,2,2-trichloroethane (hereinafter referred to as fluorocarbon 113a or 113A) with 1,1,1-trifluoro-2-chloroethane (hereinafter referred to as fluorocarbon 133a or 133A) over a solid catalyst at an elevated temperature.

1,1,1-trifluoro-2,2-dichloroethane (123) has potential as a propellent and as an intermediate to fluorocarbon 124, 1,1,1-tetrafluoro-2-monochloroethane. 1,1,1-trifluoro-2-chloroethane (133A) can be prepared in high yield and conversion by fluorination of trichloroethylene with HF over a chromium oxide or oxyfluoride and especially $Cr_2O_3$. 123 can be prepared from 133A by vapor phase-thermal chlorination (generally noncatalytic). This provides a two step process from trichloroethylene to 123. The economics of the manufacture of 123 by this chlorination process is adversely affected by the formation of 113A by-product (over chlorination). The surprising discovery that 113A can react with 133A over a suitable catalyst makes it possible to recycle this by-product. The further discovery that $Cr_2O_3$ catalyst is particularly effective in catalyzing the 113A-133A reaction opens up the possibility of recycling 113A to the first trichloroethylene fluorination reactor.

The process of this invention may be practiced by mixing gaseous fluorocarbon 133A and gaseous fluorocarbon 113A and passing the gaseous mixture into a tubular reactor heated with a suitable furnace. The tubular reactor is packed with catalyst in a granular form. The gas stream exiting the reactor may be passed through a water scrubber, an aqueous caustic scrubber, a calcium chloride drying tower and then condensed in a receiver cooled in a Dry Ice-acetone bath. The product 123 can be recovered by fractional distillation.

In practicing such a process the best results have been obtained using a $Cr_2O_3$ (Guignet Green) catalyst at 346° C., a 98 sec. contact time, and a 1:1 113A:133A molar ratio. The product mixture consisted of 14% G-123, 38% G-113A, and 46% G-133A based upon chromatographic analysis. The reaction can also be carried out over activated carbon. With activated carbon approximately 5% conversion to G-123 was observed at 357° C. Although a small amount of G-123 (approximately 1%) was formed over gamma alumina at 301° C., excessive amounts of by-product were formed. Ferric chloride on gamma alumina at 200° C. gave essentially no reaction.

The preferred catalyst for this reaction is $Cr_2O_3$ known as Guignet Green. Other chromium oxide and oxyfluoride catalysts that can be used in this invention are described in U.S. Pat. Nos. 3,258,500, 3,755,477, 3,752,850, 2,271,356, 3,859,424, 3,978,145, 3,651,156 and 3,235,612. It should be appreciated that these catalyst contain chromium at a valence state from three to six and either oxide alone or oxide and fluoride.

The catalyst may be used in fixed bed, fluidized bed or spouted bed configuration. Although less preferred, activated carbon is a suitable catalyst for this reaction.

Activated carbon can be formed from practically any organic compound capable of being carbonized. Activated carbons prepared from wood, coal, nut shells and petroleum residues are useful. Activated carbon supplied by the Union Carbide Corporation and known as Columbia activated carbon is satisfactory.

The temperature of the reactor should preferably be maintained between about 200 and about 600° C. Below about 200° C. no reaction will take place and above about 600° C. excessive breakdown occurs. The preferred range is between about 300 and about 450° C. with the most preferred range being between about 350 and about 425° C.

Contact time should preferably be between about 1 and about 600 seconds. Longer contact times become non-economical while shorter times give low conversion. The more preferred contact time is between about 30 and about 120 seconds, with the most preferred contact time being between about 60 and about 110 seconds.

The reaction may be operated at substantially atmospheric pressure or under superatmospheric pressure. The net effect of increased pressure is to increase conversion per cubic foot of catalyst per unit time and is not critical to the process.

The 113A/133A molar ratio is preferably about 1:1. No advantage accrues to using a molar excess of either reactant.

EXAMPLE 1

Catalyst Preparation

A 1 inch inside diameter 27 inch long Inconel pipe was packed with 275 cc Guignet Green $Cr_2O_3$ 6-10 mesh (American Standard) chips. The catalyst was conditioned by drying under nitrogen at 180° C. for 24 hours then for an additional 24 hours at 300° C. An $N_2$/HF gas stream was then passed over the catalyst at 300° C. for 24 hours. This treatment with HF is not essential in preparing catalyst for use in the process of this invention.

EXAMPLE 2

Reaction of Fluorocarbon 133A and Fluorocarbon 113A Over $Cr_2O_3$ 113A and 133A were passed into the reactor described in Example 1 at 346° C., each at a rate of 0.1 moles/hour, for a total of 1 hour (80 seconds contact time). Of 31.5 gm of organic feed, 25.5 gm were recovered representing an 81% organic recovery. Gas chromatography analysis of the recovered organic material indicated that the recovered organic mixture was 46.5% of 133A, 33.9% of 113A, and 14.1% of G-123, by area.

EXAMPLE 3

Reaction Over $Cr_2O_3$ at Higher Temperature 113A at 0.12 moles/hour and 133A at 0.13 moles/hour were passed into the reactor described in Example 1 at 376° C. for 1 hour (80 seconds contact time). The product mixture was determined by gas chromatography analysis to be 42.4% of 133A, 44.6% of 113A, and 12.0% of 123, by area.

EXAMPLE 4

Empty Tube 113A fed at a rate of 0.32 moles/hour and 133A fed at a rate of 0.32 moles/hour were passed into the unpacked Inconel reactor of Example 1 maintained at 350° C. Essentially no conversion to 123 product was observed.

EXAMPLE 5

Activated Carbon

The Inconel reactor of Example 1 was packed with activated carbon and maintained at 350° C. 113A and 133A were passed in, each at a rate of 0.12 moles/hour, for a total of 1 hour (contact time 91 seconds). The product mixture was determined by gas chromatography to be 48.0% of 133A, 46.6% of 113A and 4.8% of 123, by area.

EXAMPLE 6

Alumina

The reactor of Example 1 was charged with 275 cc of activated gamma alumina. The catalyst was maintained at 300° C. for 16 hours under helium purge. 113A and 133A were then passed into the reactor maintained at 301° C., each at a rate of 0.27 moles/hour. The product mixture was determined by gas chromatography to be 61.4% of 113A, 27.2% of 133A, and 1.0% of 123, and 10.3% other products, by area.

EXAMPLE 7

$FeCl_3$ on Gamma Alumina

The catalyst was prepared by soaking 500 gm of Girdler T-74 gamma alumina in an aqueous solution of 120gm of $FeCl_3$. The mixture was dryed under vacuum at between 45 and 90° C. 275 ml of this catalyst was packed into the reactor tube of Example 1 and heated under helium purge at 150-250° C. for 48 hours.

133A and 113A were passed into the reactor at 200° C., each at a rate of 0.20 moles/hour. Gas chromatography analysis of the product mixture showed 52.0% of 113A, 47.8% of 133A and no significant conversion to G-123.

We claim:

1. A process for producing 1,1,1-trifluoro-2,2-dichloroethane comprising chlorinating 1,1,1-trifluoro-2-chloroethane with $Cl_2$, recovering product 1,1,1-trifluoro-2,2-dichlorethane from the reaction mixture, reacting in the vapor phase overchlorinated byproduct 1,1,1-trifluoro-2,2,2-trichloroethane in the reaction mixture with additional 1,1,1-trifluoro-2-chloroethane in the presence of a catalyst selected from the group consisting of chromium oxides and oxyfluorides and activated carbon and recovering additional 1,1,1-trifluoro-2,2-dichloroethane from the catalyst reaction mixture.

2. The process of claim 1 wherein said chlorination is conducted in the absence of a catalyst.

3. The process of claim 1 wherein said catalyst is a chromium oxide.

4. The process of claim 3 wherein said catalyst is $Cr_2O_3$.

5. The process of claim 1 wherein said reacting step is conducted at between about 200° C. and about 600° C. with a catalyst contact time between about 1 and about 600 seconds.

6. The process of claim 5 where said reacting step is conducted at between about 300° C. and about 450° C.

7. The process of claim 6 where said reacting step is conducted at between about 350° C. and about 425° C.

8. The process of claim 5 where said contact time is between about 30 and about 120 seconds.

9. The process of claim 8 where said contact time is between about 60 and about 110 seconds.

10. The process of claim 1 wherein said reacting step is conducted at substantially atmospheric pressure.

11. The process of claim 1 where the 1,1,1-trifluoro-2-chloroethane is prepared by the fluorination of trichloroethylene with HF in the presence of a chromium oxide catalyst, and said reacting step includes reacting 1,1,1-trifluoro-2-chloroethane with 1,1,1-trifluoro-2,2,2-trichloroethane in the presence of the same chromium oxide catalyst.

12. The process of claim 11 where HF, trichloroethane and 1,1,1-trifluoro-2,2,2-trichloroethane are fed onto a chromium oxide catalyst and the 1,1,1-trifluoro-2,2,2-trichloroethane reacts with 1,1,1-trifluoro-2-chloroethane formed in situ.

13. The process of claim 11 where said chromium oxide catalyst is $Cr_2O_3$.

14. A process for producing 1,1,1-trifluoro-2,2-dichloroethane comprising reacting in the vapor phase 1,1,1-trifluoro-2-chloroethane with 1,1,1-trifluoro-2,2,2-trichloroethane in the presence of a catalyst selected from the group consisting of chromium oxides and oxyfluorides and activated carbon.

15. The process of claim 14 wherein said catalyst is a chromium oxide.

16. The process of claim 14 conducted at between about 200° C. and about 600° C. with a catalyst contact time between about 1 and about 600 seconds.

17. The process of claim 16 conducted at between about 300° C. and about 455° C.

18. The process of claim 17 conducted at between about 350° C. and about 425° C.

19. The process of claim 16 where said catalyst contact time is between about 30 and about 120 seconds.

20. The process of claim 19 where said catalyst contact time is between about 60 and about 110 seconds.

21. The process of claim 14 conducted at substantially atmospheric pressure.

* * * * *